US009956400B2

(12) United States Patent
Haasl et al.

(10) Patent No.: US 9,956,400 B2
(45) Date of Patent: May 1, 2018

(54) DELIVERY DEVICES AND METHODS FOR LEADLESS CARDIAC DEVICES

(71) Applicant: CARDIAC PACEMAKERS, INC., St. Paul, MN (US)

(72) Inventors: Benjamin J. Haasl, Forest Lake, MN (US); Brian L. Schmidt, White Bear Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 0 days. days.

(21) Appl. No.: 14/919,310

(22) Filed: Oct. 21, 2015

(65) Prior Publication Data

US 2016/0114157 A1 Apr. 28, 2016

Related U.S. Application Data

(60) Provisional application No. 62/067,140, filed on Oct. 22, 2014.

(51) Int. Cl.
*A61N 1/05* (2006.01)
*A61N 1/375* (2006.01)
*A61N 1/372* (2006.01)

(52) U.S. Cl.
CPC ......... *A61N 1/0587* (2013.01); *A61N 1/3756* (2013.01); *A61N 1/37205* (2013.01); *A61N 2001/058* (2013.01)

(58) Field of Classification Search
CPC .............. A61N 1/0587; A61N 1/37205; A61N 1/3756; A61N 2001/058; A61B 17/3468
USPC .......................................................... 607/119
See application file for complete search history.

(56) References Cited

U.S. PATENT DOCUMENTS

| | | |
|---|---|---|
| 4,301,815 A | 11/1981 | Doring |
| 5,238,004 A | 8/1993 | Sahatjian et al. |
| 5,807,399 A | 9/1998 | Laske et al. |
| 5,908,381 A | 6/1999 | Aznoian et al. |
| 6,181,973 B1 | 1/2001 | Ceron et al. |
| 6,395,017 B1 | 5/2002 | Dwyer et al. |
| 6,409,674 B1 | 6/2002 | Brockway et al. |
| 6,508,803 B1 | 1/2003 | Horikawa et al. |
| 6,582,441 B1 | 6/2003 | He et al. |
| 6,638,268 B2 | 10/2003 | Niazi |

(Continued)

FOREIGN PATENT DOCUMENTS

WO     2012082735 A1     6/2012

*Primary Examiner* — Carl H Layno
*Assistant Examiner* — Erin M Piateski
(74) *Attorney, Agent, or Firm* — Seager, Tufte & Wickhem LLP

(57) ABSTRACT

Delivery devices, systems, and methods for delivering implantable leadless pacing devices are disclosed. An example delivery device may an outer tubular member and an inner tubular member slidably disposed within the lumen of the outer tubular member. A distal holding section may extend distally of a distal end of the inner tubular member and define a cavity therein for receiving an implantable leadless pacing device. The device may further include a hub portion including at least a first hub portion affixed adjacent to the proximal end of the outer tubular member and a second hub portion affixed adjacent to the proximal end of the inner tubular member. A first locking mechanism configured to releasably couple the outer tubular member and the inner tubular member may be disposed within the hub portion.

20 Claims, 8 Drawing Sheets

(56) References Cited

U.S. PATENT DOCUMENTS

| | | |
|---|---|---|
| 6,786,918 B1 | 9/2004 | Krivoruchko et al. |
| 7,381,216 B2 | 6/2008 | Buzzard et al. |
| 7,499,758 B2 | 3/2009 | Cates et al. |
| 7,608,099 B2 | 10/2009 | Johnson et al. |
| 7,799,037 B1 | 9/2010 | He et al. |
| 7,840,281 B2 | 11/2010 | Kveen et al. |
| 7,993,351 B2 | 8/2011 | Worley et al. |
| 8,010,209 B2 | 8/2011 | Jacobson |
| 8,103,361 B2 | 1/2012 | Moser |
| 8,185,213 B2 | 5/2012 | Kveen et al. |
| 8,267,987 B2 | 9/2012 | Johnson et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,428,750 B2 | 4/2013 | Kolberg |
| 8,478,431 B2 | 7/2013 | Griswold et al. |
| 8,504,156 B2 | 8/2013 | Bonner et al. |
| 8,527,068 B2 | 9/2013 | Ostroff |
| 8,532,790 B2 | 9/2013 | Griswold |
| 8,548,605 B2 | 10/2013 | Ollivier |
| 8,615,310 B2 | 12/2013 | Khairkhahan et al. |
| 8,634,912 B2 | 1/2014 | Bomzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,855,789 B2 | 10/2014 | Jacobson |
| 8,903,513 B2 | 12/2014 | Dllivier |
| 8,926,588 B2 | 1/2015 | Berthiaume et al. |
| 8,945,145 B2 | 2/2015 | Tran et al. |
| 8,945,146 B2 | 2/2015 | Steingisser et al. |
| 8,948,883 B2 | 2/2015 | Eggen et al. |
| 8,958,892 B2 | 2/2015 | Khairkhahan et al. |
| 9,020,611 B2 | 4/2015 | Khairkhahan et al. |
| 9,072,872 B2 | 7/2015 | Asleson et al. |
| 9,101,281 B2 | 8/2015 | Reinert et al. |
| 9,119,959 B2 | 9/2015 | Rys et al. |
| 9,126,032 B2 | 9/2015 | Khairkhahan et al. |
| 9,205,225 B2 | 12/2015 | Khairkhahan et al. |
| 2001/0052345 A1 | 12/2001 | Niazi |
| 2004/0019359 A1 | 1/2004 | Worley et al. |
| 2004/0193180 A1 | 9/2004 | Buzzard et al. |
| 2004/0230280 A1 | 11/2004 | Cates et al. |
| 2005/0267555 A1 | 12/2005 | Marnfeldt et al. |
| 2006/0200222 A1 | 9/2006 | Johnson et al. |
| 2007/0088418 A1 | 4/2007 | Jacobson |
| 2007/0191864 A1 | 8/2007 | Shumer |
| 2007/0233218 A1 | 10/2007 | Kolberg |
| 2008/0021532 A1 | 1/2008 | Kveen et al. |
| 2009/0082828 A1 | 3/2009 | Ostroff |
| 2009/0281605 A1 | 11/2009 | Marnfeldt et al. |
| 2010/0004732 A1 | 1/2010 | Johnson et al. |
| 2010/0198288 A1 | 8/2010 | Ostroff |
| 2010/0274227 A1 | 10/2010 | Khairkhahan et al. |
| 2011/0009944 A1 | 1/2011 | Moser |
| 2011/0034939 A1 | 2/2011 | Kveen et al. |
| 2011/0112548 A1 | 5/2011 | Fifer et al. |
| 2011/0237967 A1 | 9/2011 | Moore et al. |
| 2011/0238077 A1 | 9/2011 | Wenger |
| 2011/0251660 A1 | 10/2011 | Griswold |
| 2011/0251662 A1 | 10/2011 | Griswold et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0095539 A1 | 4/2012 | Khairkhahan et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0290066 A1* | 11/2012 | Nabulsi .................. A61F 2/966 623/1.11 |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1* | 4/2013 | Steingisser .......... A61N 1/3756 606/129 |
| 2013/0116741 A1 | 5/2013 | Bomzin et al. |
| 2013/0131591 A1 | 5/2013 | Berthiaume et al. |
| 2013/0131693 A1 | 5/2013 | Berthiaume et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1* | 9/2013 | Griswold ............ A61N 1/37205 600/486 |
| 2014/0018818 A1 | 1/2014 | Somogyi et al. |
| 2014/0031836 A1 | 1/2014 | Ollivier |
| 2014/0058494 A1 | 2/2014 | Ostroff et al. |
| 2014/0074114 A1 | 3/2014 | Khairkhahan et al. |
| 2014/0148815 A1 | 5/2014 | Wenzel et al. |
| 2014/0180306 A1 | 6/2014 | Grubac et al. |
| 2014/0249543 A1 | 9/2014 | Berthiaume et al. |
| 2014/0257324 A1 | 9/2014 | Fain |
| 2014/0303704 A1 | 10/2014 | Suwito et al. |
| 2014/0324145 A1 | 10/2014 | Eggen et al. |
| 2014/0378991 A1 | 12/2014 | Ollivier |
| 2015/0039069 A1 | 2/2015 | Rys et al. |
| 2015/0039070 A1 | 2/2015 | Kuhn et al. |
| 2015/0039071 A1 | 2/2015 | Grubac et al. |
| 2015/0045868 A1 | 2/2015 | Bonner et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051682 A1 | 2/2015 | Schmidt et al. |
| 2015/0094668 A1 | 4/2015 | Wood et al. |
| 2015/0094735 A1 | 4/2015 | Ward et al. |
| 2015/0112361 A1 | 4/2015 | Khairkhahan et al. |
| 2015/0148815 A1 | 5/2015 | Steingisser et al. |
| 2015/0151117 A1 | 6/2015 | Eggen et al. |
| 2015/0273207 A1 | 10/2015 | Tran et al. |
| 2015/0273212 A1 | 10/2015 | Berthiaume et al. |
| 2015/0297899 A1 | 10/2015 | Ostroff |
| 2015/0335884 A1 | 11/2015 | Khairkhahan et al. |
| 2015/0352351 A1 | 12/2015 | Muessig et al. |
| 2015/0352353 A1 | 12/2015 | Rys et al. |
| 2016/0000563 A1 | 1/2016 | Asleson et al. |

* cited by examiner

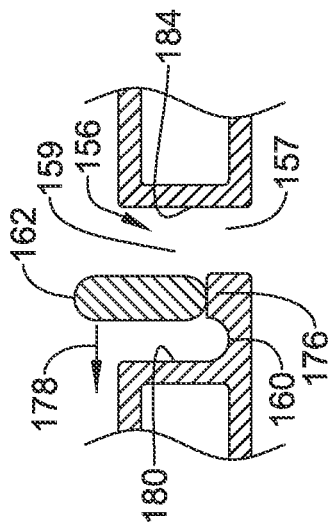
FIG. 6B
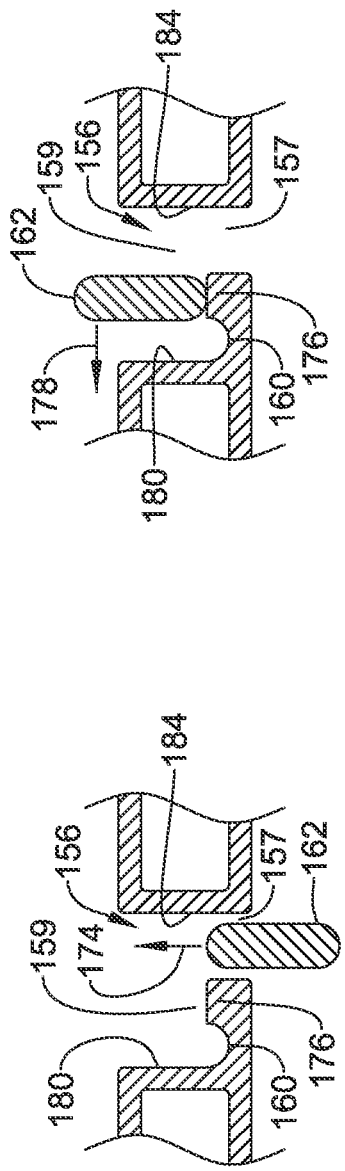
FIG. 6A
FIG. 6C
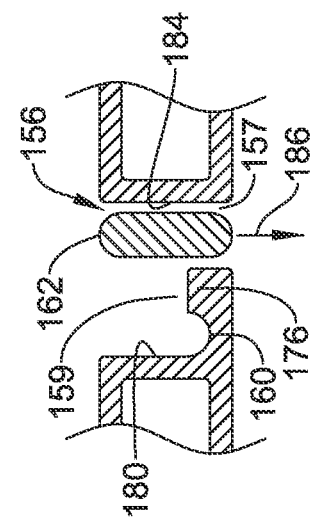
FIG. 6E
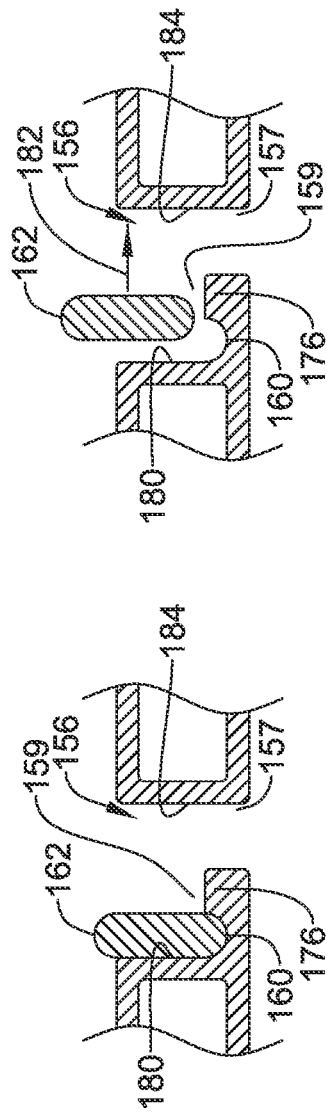
FIG. 6D

DELIVERY DEVICES AND METHODS FOR LEADLESS CARDIAC DEVICES

CROSS-REFERENCE TO RELATED APPLICATIONS

This application claims priority under 35 U.S.C. § 119 to U.S. Provisional Application Ser. No. 62/067,140, filed Oct. 22, 2014, the entirety of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices.

In a first example, a delivery device for delivering an implantable leadless pacing device may comprise an outer tubular member including a lumen extending from a proximal end to a distal end thereof, an inner tubular member including a lumen extending from a proximal end to a distal end thereof, the inner tubular member slidably disposed within the lumen of the outer tubular member, a distal holding section extending distally of a distal end of the inner tubular member, the distal holding section defining a cavity therein for receiving an implantable leadless pacing device, a handle assembly including at least a first hub portion affixed adjacent to the proximal end of the outer tubular member and intermediate second hub portion affixed adjacent to the proximal end of the inner tubular member, and a first locking mechanism disposed within the handle assembly, wherein the first locking mechanism is configured to releasably couple the first hub portion and the second hub portion.

Alternatively or additionally to any of the examples above, in another example, the first locking mechanism may have a locked position and an unlocked position wherein the inner tubular member is held in tension in the locked position.

Alternatively or additionally to any of the examples above, in another example, the outer tubular member may be held in compression in the locked position.

Alternatively or additionally to any of the examples above, in another example, the first hub portion and the second hub portion may be individually slidable and rotatable when the first locking mechanism is in an unlocked configuration.

Alternatively or additionally to any of the examples above, in another example, the first locking mechanism may be selected from the group of a snap lock, a threaded engagement, or a quick connect locking feature.

Alternatively or additionally to any of the examples above, in another example, the first locking mechanism may comprise a bayonet style locking mechanism.

Alternatively or additionally to any of the examples above, in another example, the second hub portion may comprise a groove positioned adjacent a distal end of the second hub portion, the groove configured to receive an inwardly extending protrusion of the first hub portion.

Alternatively or additionally to any of the examples above, in another example, the groove may comprise a first portion, a second portion extending generally orthogonal to the first portion, and a serif positioned at an end of the second portion.

Alternatively or additionally to any of the examples above, in another example, disposing the protrusion within the serif may releasably couple the outer tubular member and the inner tubular member such that longitudinal or rotational actuation of either of the outer tubular member or the inner tubular member results in corresponding actuation of both the outer tubular member and the inner tubular member.

Alternatively or additionally to any of the examples above, in another example, disposing the protrusion within the serif may place the inner tubular member in tension and the outer tubular member in compression.

Alternatively or additionally to any of the examples above, in another example, the device may further comprise a push member slidably disposed within the lumen of the inner tubular member.

Alternatively or additionally to any of the examples above, in another example, the device may further comprise a third hub portion affixed adjacent to a proximal end of the push member.

Alternatively or additionally to any of the examples above, in another example, the device may further comprise a second locking mechanism disposed within the handle assembly.

Alternatively or additionally to any of the examples above, in another example, the third hub portion may be slidable and rotatable independent of either of the first hub portion or the second hub portion when the second locking mechanism is in an unlocked configuration.

Alternatively or additionally to any of the examples above, in another example, longitudinal or rotational actuation of either of the inner tubular member or the push member may result in corresponding actuation of both the inner tubular member and the push member when the second locking mechanism is in a locked configuration.

Alternatively or additionally to any of the examples above, in another example, a method of releasably coupling an outer tubular member affixed to a first hub portion to an inner tubular member affixed to a second hub portion of a delivery device may comprise rotating the second hub portion relative to the first hub portion, the first hub portion having an inwardly extending protrusion, to align the protrusion with a first portion of a groove on a distal portion of the second hub portion, proximally retracting the second hub portion to advance the protrusion into the first portion of the groove, rotating the second hub portion relative to the first hub portion about a longitudinal axis of the first hub portion to advance the protrusion along a second portion of the groove, the second portion of the groove extending generally orthogonal to the first portion of the groove, and disposing the protrusion within a serif positioned at an end of the second portion of the groove.

Alternatively or additionally to any of the examples above, in another example, a delivery device for delivering an implantable leadless pacing device may comprise an outer tubular member including a lumen extending from a proximal end to a distal end thereof, an inner tubular member including a lumen extending from a proximal end to a distal end thereof, the inner tubular member slidably disposed within the lumen of the outer tubular member, a distal holding section extending distally of a distal end of the inner tubular member, the distal holding section defining a cavity therein for receiving an implantable leadless pacing device, a handle assembly including at least a first hub portion affixed adjacent to the proximal end of the outer tubular member and a second hub portion affixed adjacent to the proximal end of the inner tubular member, and a first locking mechanism disposed within the handle assembly, wherein the first locking mechanism is configured to releasably couple the first hub portion and the second hub portion.

Alternatively or additionally to any of the examples above, in another example, the first locking mechanism may have a locked position and an unlocked position wherein the inner tubular member is held in tension in the locked position.

Alternatively or additionally to any of the examples above, in another example, the outer tubular member may be held in compression in the locked position.

Alternatively or additionally to any of the examples above, in another example, the first hub portion and the second hub portion may be individually slidable and rotatable when the first locking mechanism is in an unlocked configuration.

Alternatively or additionally to any of the examples above, in another example, the first locking mechanism may comprise a bayonet style locking mechanism.

Alternatively or additionally to any of the examples above, in another example, the second hub portion may comprise a groove positioned adjacent a distal end of the second hub portion, the groove configured to receive an inwardly extending protrusion of the first hub portion.

Alternatively or additionally to any of the examples above, in another example, the groove may comprise a first portion, a second portion extending generally orthogonal to the first portion, and a serif positioned at an end of the second portion.

Alternatively or additionally to any of the examples above, in another example, disposing the protrusion within the serif may releasably couple the outer tubular member and the inner tubular member such that longitudinal or rotational actuation of either of the outer tubular member or the inner tubular member results in corresponding actuation of both the outer tubular member and the inner tubular member.

Alternatively or additionally to any of the examples above, in another example, disposing the protrusion within the serif may place the inner tubular member in tension and the outer tubular member in compression.

Alternatively or additionally to any of the examples above, in another example, the device may further comprise a push member slidably disposed within the lumen of the inner tubular member.

Alternatively or additionally to any of the examples above, in another example, the device may further comprise a third hub portion affixed adjacent to a proximal end of the push member.

Alternatively or additionally to any of the examples above, in another example, the device may further comprise a second locking mechanism disposed within the handle assembly.

Alternatively or additionally to any of the examples above, in another example, the third hub portion may be slidable and rotatable independent of either of the first hub portion or the second hub portion when the second locking mechanism is in an unlocked configuration.

Alternatively or additionally to any of the examples above, in another example, the first locking mechanism may be selected from the group of a snap lock, a threaded engagement, or a quick connect locking feature.

Alternatively or additionally to any of the examples above, in another example, longitudinal or rotational actuation of either of the inner tubular member or the push member may result in corresponding actuation of both the inner tubular member and the push member when the second locking mechanism is in a locked configuration.

Alternatively or additionally to any of the examples above, in another example, a delivery device for delivering an implantable leadless pacing device may comprise an outer tubular member including a lumen extending from a proximal end to a distal end thereof, an inner tubular member including a lumen extending from a proximal end to a distal end thereof, the inner tubular member slidably disposed within the lumen of the outer tubular member, a push member having a proximal end and a distal end, the push member slidably disposed within the lumen of the inner tubular member, a distal holding section extending distally of a distal end of the inner tubular member, the distal holding section defining a cavity therein for receiving an implantable leadless pacing device, a handle assembly including a distal hub portion affixed adjacent to the proximal end of the outer tubular member, an intermediate hub portion affixed adjacent to the proximal end of the inner tubular member, and a proximal hub portion affixed adjacent to the proximal end of the push member, the distal hub portion, the intermediate hub portion, and the proximal hub portion arranged in a telescoping configuration such that each of the distal hub portion, intermediate hub portion, and proximal hub portion are capable of being longitudinally and rotationally actuated individually, and a first locking mechanism disposed between the distal hub portion and the intermediate hub portion, wherein the first locking mechanism is configured to releasably couple the distal hub portion and the intermediate hub portion.

Alternatively or additionally to any of the examples above, in another example, the first locking mechanism may be user actuatable between an unlocked configuration and a locked configuration.

Alternatively or additionally to any of the examples above, in another example, when in the locked configuration, the intermediate hub portion may be proximally retracted to place the inner tubular member in tension and the outer tubular member in compression.

Alternatively or additionally to any of the examples above, in another example, a method of releasably coupling an outer tubular member affixed to a first hub portion and an inner tubular member affixed to a second hub portion of a delivery device may comprise rotating a the first hub portion in a first direction relative to the second hub portion, the first hub portion having an inwardly extending protrusion, to align the protrusion with a first portion of a groove on a distal portion of a second hub portion, advancing the protrusion into the first portion of the groove, rotating the second hub portion relative to the first hub portion and about a longitudinal axis of the first hub portion in a first direction to advance the protrusion along a second portion of the groove, the second portion of the groove extending generally orthogonal to the first portion of the groove, and disposing the protrusion within a serif positioned at an end of the second portion of the groove.

Alternatively or additionally to any of the examples above, in another example, disposing the protrusion within the serif may releasably couple the inner tubular member and the outer tubular member such that longitudinal or rotational actuation of either of the outer tubular member or the inner tubular member results in corresponding actuation of both the outer tubular member and the inner tubular member.

Alternatively or additionally to any of the examples above, in another example, the method may further comprise disengaging the protrusion from the serif, rotating the second hub portion relative to the first hub portion in a second direction, the second direction generally opposite to the first direction, to advance the protrusion along a second portion of the groove towards the first portion of the groove, and distally advancing the second hub portion to disengage the protrusion from the first portion of the groove, wherein disengaging the protrusion from the first portion of the groove uncouples the inner tubular member and the outer tubular member.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which:

FIGS. 6A-6E are a schematic view of a locking mechanism of the proximal portion of the delivery device of FIG. 2.

Figure 1:
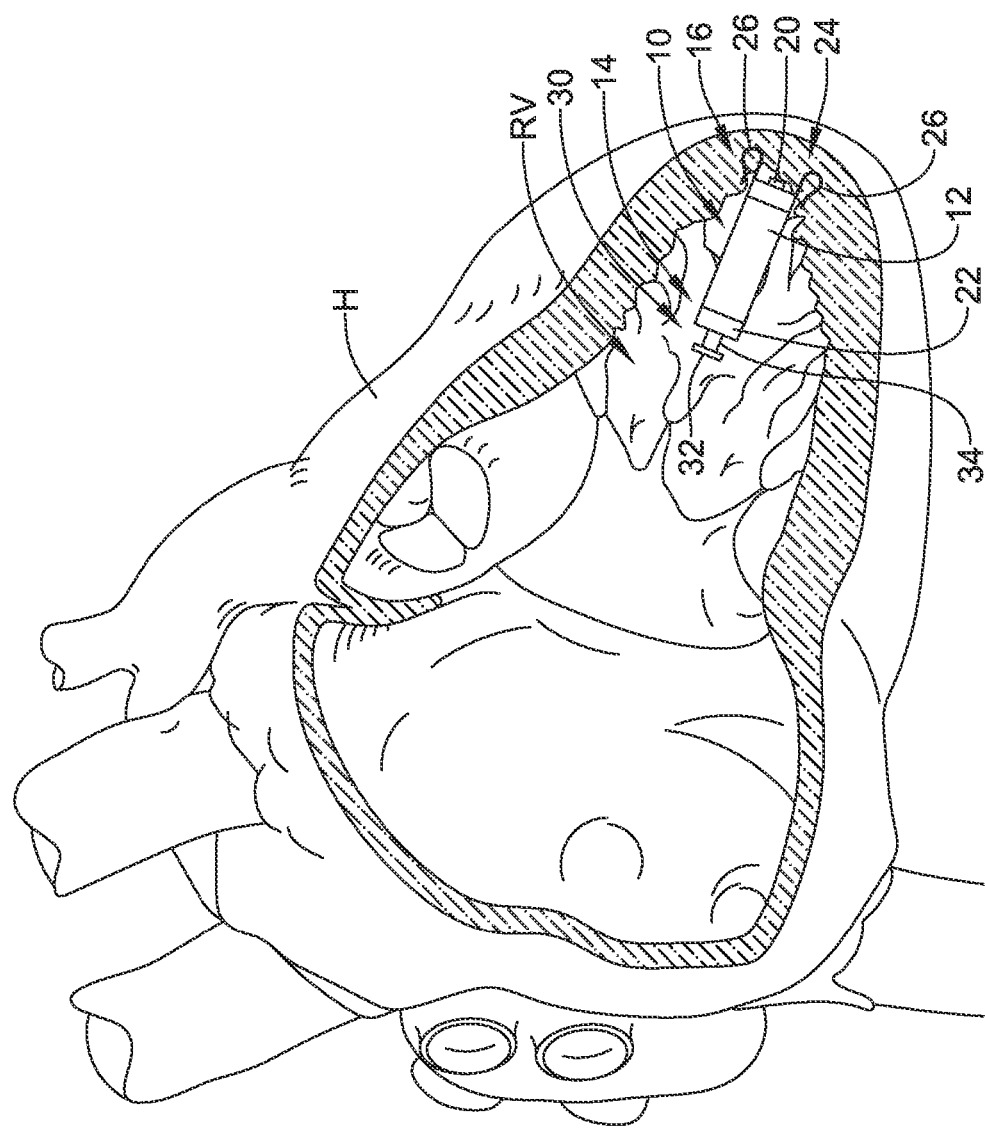
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition. The capsule may be delivery to the heart using a delivery device which may be advanced through a femoral vein, into the inferior vena cava, into the right atrium, through the tricuspid valve, and into the right ventricle. Accordingly, it may be desirable to provide delivery devices which facilitate advancement through the vasculature.

FIG. 1 illustrates an example implantable leadless cardiac pacing device 10 (e.g., a leadless pacemaker) implanted in a chamber of a heart H, such as the right ventricle RV. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be capable of being positioned against or may otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion from the longitudinal axis of the implantable device 10. The docking member 30 may be configured to facilitate delivery of the implantable device 10 to the intracardiac site and/or retrieval of the implantable device 10 from the intracardiac site. Other docking members 30 are contemplated.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes.

Figure 2:
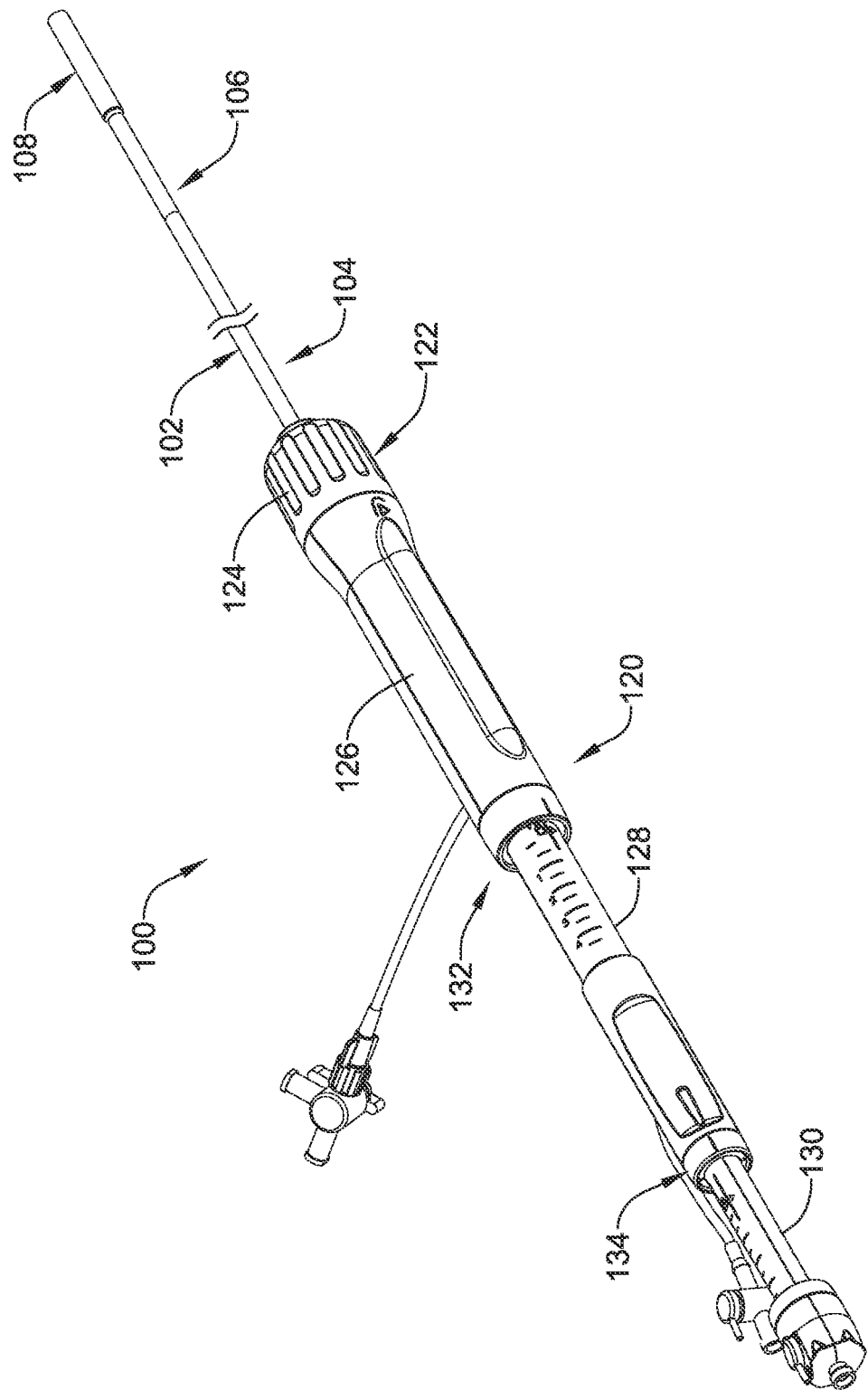
FIG. 2 is a perspective view of an example delivery device for an implantable leadless cardiac pacing device.

FIG. 2 is a perspective view of an illustrative delivery device 100, such as a catheter, that may be used to deliver the device 10. The delivery device 100 may include an outer tubular member 102 having a proximal section 104 and a distal section 106. An inner tubular member 110 may be slidably disposed within a lumen 150 of the outer tubular member 102 (see e.g. FIGS. 3 and 4). A distal holding section 108 may be attached to a distal end portion 114 of the inner tubular member 110. The delivery device 100 may also include a handle assembly 120 positioned adjacent to the proximal section of the outer tubular member 102. In some embodiments, the outer tubular member 102 may include at least a section thereof that has an outer diameter D2 that is less than the outer diameter D1 of at least a portion of the holding section 108 (see e.g. FIG. 3).

Figure 3:
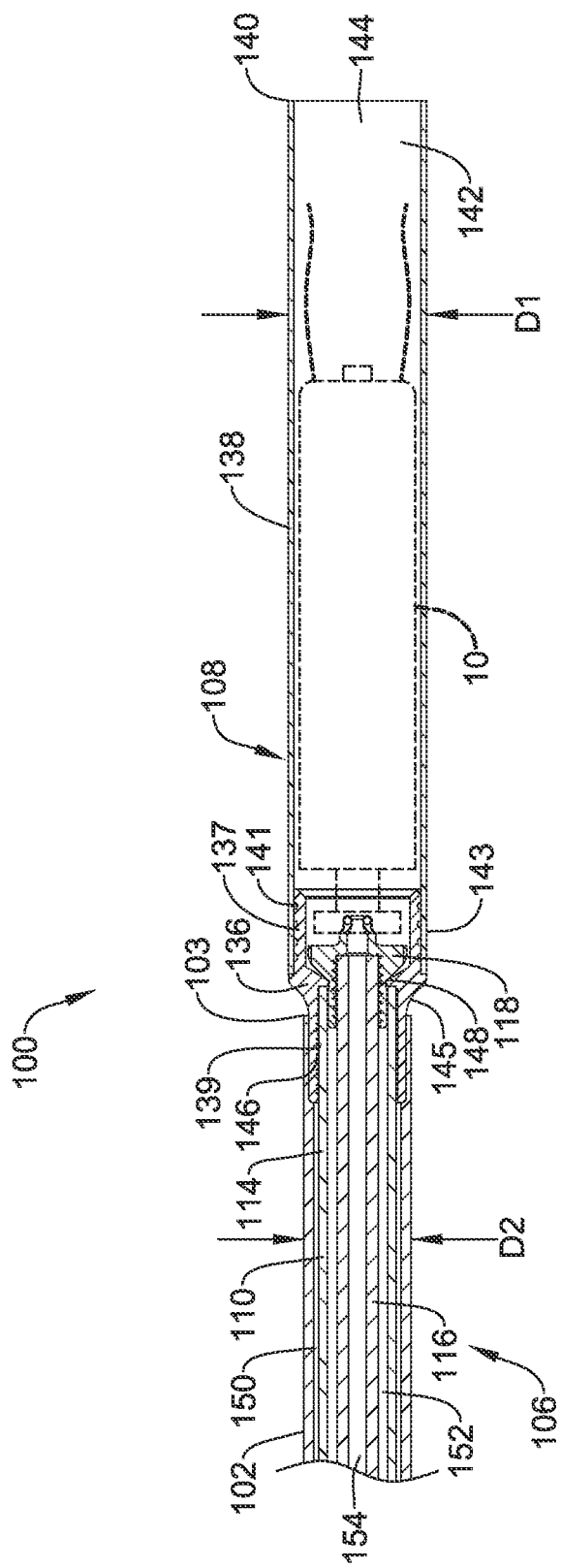
FIG. 3 is a partial cross-sectional side view of the distal portion of the delivery device of FIG. 2.

The handle assembly 120 may include a first or distal hub portion 126 attached to the proximal end section 104 of the outer tubular member 102, a second or intermediate hub portion 128 attached to a proximal end section of the inner tubular member 110, and a third or proximal hub portion 130 attached to a proximal end section of a push member 116 (see e.g. FIG. 3). The first hub portion 126, second hub portion 128, and third hub portion 130 may be positioned in a generally telescoping arrangement and slidable relative to each other. As will be discussed in more detail below, each of the first hub portion 126, the second hub portion 128, and the third hub portion 130 may be slidable and rotatable relative to each other such that the outer tubular member 102, inner tubular member 110, and push member 116 may be individually actuated. In some instances, it may be desirable to move the outer tubular member 102, inner tubular member 110 and push member 116 simultaneously. The handle assembly 120 may include a first locking mechanism 132 to releasably couple the outer tubular member 102 to the inner tubular member 110, as will be discussed in more detail below. The handle assembly 120 may also include a second locking mechanism 134 to releasably couple the inner tubular member 110 to the push member 116, as will be discussed in more detail below.

The distal holding section 108 may be configured to receive the implantable device 10 therein. For example, referring to FIG. 3, which illustrates a cross-sectional view of a distal portion of delivery device 100, the holding section 108 may define a cavity 142 for slidably receiving the implantable device 10, and may include a distal opening 144 for slidable insertion and/or extraction of the implantable device 10 into and/or out of the cavity 142.

The distal holding section 108 may include a body portion 138 and a distal tip portion 140 that may be, for example, configured to be atraumatic to anatomy, such as a bumper tip. For example, as the catheter is navigated through the anatomy, the distal tip may come into contact with anatomy. Additionally, when the catheter is used to deliver the device, the tip 140 of the delivery device 100 will likely come into contact with tissue adjacent the target cite (e.g. cardiac tissue of the heart). A hard distal tip formed of the material of the outer tubular member 102 and/or inner tubular member 110 may injure a vessel wall or cardiac tissue. As such, it may be desirable to provide the delivery device 100 with a softer distal tip 140 that can be introduced into the anatomy and come into contact with anatomy adjacent the target cite without causing unnecessary trauma.

For example, the distal tip 140 may be made of a material that is softer than the body portion 138 of the distal holding section. In some cases, the distal tip 140 may include a material that has a durometer that is less than the durometer of the material of the body portion 138. In some particular embodiments, the durometer of the material used in the distal tip 140 may be in the range of about 5 D to about 70 D, or for example, in the range of about 25 D to about 65 D. Additionally, the distal tip 140 may include a shape or structure that may make it less traumatic to tissue. For example, the distal tip 140 may have a distal surface, such as a tissue contacting surface, that is that is rounded or includes a curvature configured to be more atraumatic to tissue.

In some embodiments, all or a portion of the distal holding section 108 may include an inner surface that may be configured to resist getting caught on the fixation mechanism 24, such as the one or more, or a plurality of hooks 26 on the device 10. For example, the distal holding section 108 may include an inner layer or coating of harder or more lubricious material that resists force applied by the fixation mechanism 24 onto the inner surface of the distal holding section 108. For example, the distal holding section 108 may include a multi-layered structure, and an inner layer may be made of a material that is harder than an outer layer.

A push member 116 may be disposed (e.g., slidably disposed) within a lumen 152 of the inner tubular member 110. The push member 116 may be engaged by a user near or at the third hub portion 130, and extend through a lumen 152 of the inner tubular member 110 and into the distal holding section 108. A distal portion 118 of the push member 116 may be capable of engaging the device 10, and the push member 116 may be used to "push" the device 10 out from distal holding section 108 so as to deploy and anchor device 10 within a target region (e.g., a region of the heart such as the right ventricle).

In order to more specifically place or steer the delivery device 100 to a position adjacent to the intended target, the delivery device 100 may be configured to be deflectable or articulable or steerable. Referring to FIG. 2, for example, the outer tubular member 102 and/or inner tubular member 110 may include one or more articulation or deflection mechanism(s) that may allow for the catheter 100, or portions thereof, to be deflected, articulated, steered and/or controlled in a desired manner. For example, the outer tubular member 102 may include at least a portion thereof that can be selectively bent and/or deflected in a desired or predetermined direction. This may, for example, allow a user to orient the delivery device 100 such that the holding section 108 is in a desirable position or orientation for navigation or delivery of the device 10 to a target location. The outer tubular member 102 may be deflected, for example, along a deflection region.

A wide variety of deflection mechanisms may be used. In some example embodiments, deflection may be effected by one or more actuation members, such as pull wire(s) extending between a distal portion of the outer tubular member 102 and an actuation mechanism 122 near the proximal end of the outer tubular member 102. As such, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and thereby deflect or bend the outer tubular member 102 in a desired manner. In addition, in some cases the one or more wires may be stiff enough so that they can also be used to provide a pushing and/or tensioning force on the outer tubular member 102, for example, to "push" or "straighten" the shaft into a desired position or orientation.

In some embodiments, the actuation member takes the form of a continuous wire that is looped through or otherwise coupled to a distal end region of the outer tubular member 102 so as to define a pair of wire sections. Other embodiments are contemplated, however, including embodiments where the actuation member includes one or a plurality of individual wires that are attached, for example, to a metal or metal alloy ring adjacent the distal end region of the outer tubular member 102.

The actuation mechanism 122 may include a desired mechanism that may allow for applying tension (i.e. pulling force), or compression (i.e. pushing force), or both, on the actuation member(s). In some embodiments, the actuation mechanism 122 may include an external rotatable member 124 connected to and rotatable about the longitudinal axis of the handle assembly 120. The rotatable member 124 may threadingly engage an internal member that is attached to the proximal end of the actuation member(s) or pull wires. When the external rotatable member 124 is rotated in a first rotational direction, the internal member translates in a first longitudinal direction, thereby applying tension to the pull wires, which applies compression force to the shaft, so as to deflect the outer tubular member 102 from an initial position to a deflected position. When the external rotatable member 124 is rotated in a second rotational direction, the internal member translates in a second longitudinal direction, thereby releasing the tension on the pull wires, and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wires, such that the wires may apply tension to the outer tubular member 102 and "push" the outer tubular member 102 back toward an initial position, and possibly into additional positions beyond the initial position.

The one or more articulation and/or deflection mechanism(s) may also entail the outer tubular member 102 including structure and/or material that may provide for the desired degree and/or location of the deflection when the compressive or tensile forces are applied. For example, the outer tubular member 102 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102.

In other embodiments, other articulation and/or deflection mechanism(s) are contemplated. For example, all or a portion of the delivery device 100, such as the outer tubular member 102, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material and mechanism may be used to deflect or bend the outer tubular member 102 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 may include one or more predefined or fixed curved portion(s) along the length thereof. In some cases, such curved sections may be configured to fit with particular anatomies or be configured for better navigation or delivery of the device 10. Additionally, or alternatively, some such curved sections may be configured to allow the outer tubular member 102 to be predisposed to be bent and/or deflected in a certain direction or configuration when compression and/or tension forces are applied thereto.

Returning again to FIG. 3, the distal holding section 108 may be affixed to a distal end portion 114 of the inner tubular member 110. The distal holding section 108 may include a hub portion 136 and a tubular body portion 138. In some instances, the hub portion 136 may be formed from a metal or metal alloy while the body portion 138 may be formed from a polymeric material, although this is not required. In some instances, a proximal region 143 of the body portion 138 may be heat bonded to a distal end portion 137 of the hub portion 136, or otherwise affixed. As the body portion 138 is heated, the body portion 138 may reflow into grooves 141 in the distal end portion 137. The hub portion 136 may include a tapered intermediate region 145 disposed between a proximal end portion 139 and the distal end portion 137.

In some embodiments, the outer tubular member 102 may include a metal ring or tip adjacent the distal end 103 thereof for attaching one or more pull wires thereto. It is contemplated that the outer tubular member 102 may further include a lubricious liner, such as, but not limited to a polytetrafluoroethylene (PTFE) liner. The proximal end portion 139 of the hub portion 136 may extend proximally into the lumen 150 of the outer tubular member 102. In some instances, an outer surface of the proximal end portion 139 may form an interference fit with an inner surface of the outer tubular member 102. It is contemplated that the outer surface of the proximal end portion 139 and the inner surface of the outer tubular member 102 may be coupled in a tapered engagement. For example, the distal end 103 of the outer tubular member 102 may flare radially outwards in the distal direction and/or the proximal end portion 139 may taper radially inward in the proximal direction. The two angled surface may engage as the proximal end portion 139 is proximally retracted within the outer tubular member 102. Other coupling arrangements may be used as desired.

Figure 3A:
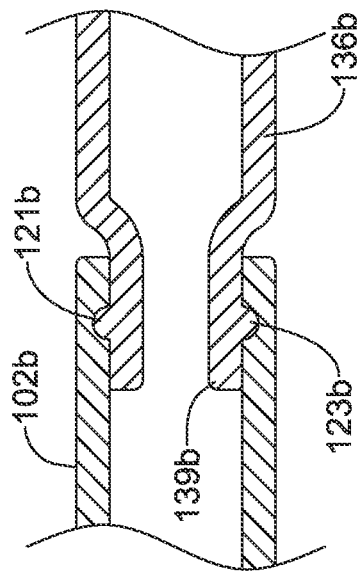
FIG. 3A is a partial cross-sectional side view of a portion of a distal portion of another illustrative delivery device.

FIG. 3A illustrates a partial cross-sectional view of an alternative mechanism for coupling the outer tubular member 102a to the proximal end 139a of the hub portion 136a. Some components have been removed for clarity. The outer tubular member 102a and the hub portion 136a may be similar in form and function to the outer tubular member 102 and the hub portion 136 described above. In some instances, the outer tubular member 102a and the proximal end portion 139a may be coupled through a threaded engagement. For example, the outer tubular member 102a may include a first helical flange or threaded portion 125a and the proximal end portion 139a may include a second helical flange or threaded portion 127a configured to mate with and/or threadably engage the helical flange or threaded portion 125a on the outer tubular member 102a. It is contemplated that the outer tubular member 102a and/or the hub portion 136a may be rotated in a first direction causing helical flanges or threaded portions 125a, 127a to engage. Rotation of the outer tubular member 102a and/or the hub portion 136a in a second direction opposite the first direction may cause the helical flanges or threaded portions 125a, 127a to disengage.

Figure 3B:
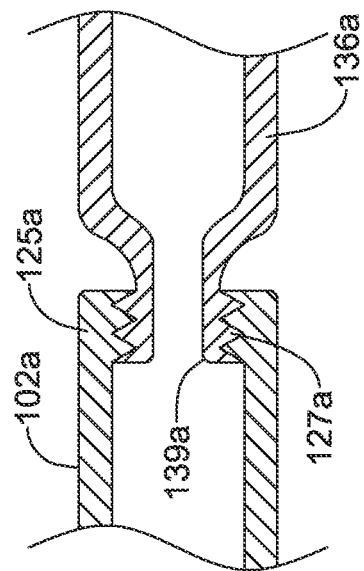
FIG. 3B is a partial cross-sectional side view of a portion of a distal portion of another illustrative delivery device.

FIG. 3B illustrates a partial cross-sectional view of an alternative mechanism for coupling the outer tubular member 102b to the proximal end 139b of the hub portion 136b. The outer tubular member 102b and the hub portion 136b may be similar in form and function to the outer tubular member 102 and the hub portion 136 described above. The coupling arrangement may include a snap lock, a tongue and groove type lock, a mating detent and groove or other features configured to engage a corresponding feature on the outer tubular member 102b and/or the proximal end portion 139b. For example, the outer tubular member 102b may include a groove or recess 121b disposed in an inner wall thereof. The proximal end 139b may include a protrusion, bump, or other extending feature 123b configured to mate or engage with the recess 121b in the outer tubular member 102b. It is contemplated that the protrusion 123b and the groove 121b may be disengaged through application of an external force (e.g., axial force) such as proximal refraction of the outer tubular member 102b and/or distal actuation of the hub portion 136b.

Figure 3C:
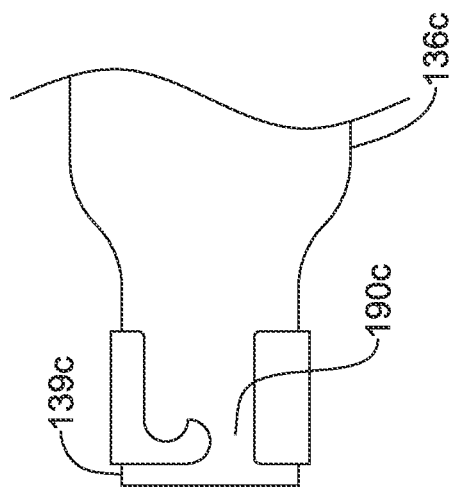
FIG. 3C is a partial perspective view of a portion of a distal portion of another illustrative delivery device.
Figure 3C:
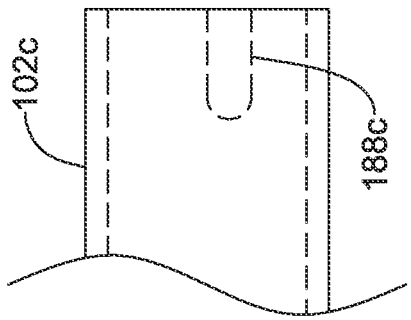

FIG. 3C illustrates a perspective view of another alternative mechanism for coupling the outer tubular member 102c to the proximal end 139c of the hub portion 136c. The outer tubular member 102c and the hub portion 136c may be similar in form and function to the outer tubular member 102 and the hub portion 136 described above. In some embodiments, the outer tubular member 102c and the proximal end portion 139c may be coupled through a bayonet style locking feature. It is contemplated that a generally "L" shaped groove 190c may be formed in the proximal end 139c of the hub portion 136c. In some instances, the outer tubular member 102c may include a protrusion 188c extending radially inward from an inner surface of the outer tubular member 102c. The "L" shaped groove 190c and the protrusion 188c may be configured to releasably engage one another in a manner similar the locking mechanism 132 described with respect to FIGS. 6A-6E such that the outer tubular member 102c and the proximal end 139c of the hub portion 136c may be releasably coupled. Alternatively, a generally "L" shaped groove may be formed in the distal end of the outer tubular member 102c and the proximal end 139c of the hub portion 136c may include a protrusion extending radially outward therefrom for mating engagement with the groove.

It is contemplated that as the outer tubular member 102 is bent to navigate the implantable device 10 to the desired location, the proximal end portion 139 may advance distally and disengage from the inner surface of the outer tubular member 102 creating a kink point or weakened region adjacent to the bonding region 146. Proximally retracting the inner tubular member 110 to bring the intermediate region 145 into contact with the outer tubular member 102 at contact point 148 and/or bringing the proximal end portion 139 into the outer tubular member 102 and fixing the inner tubular member 110 in this configuration may help prevent migration of the distal holding section 108 during navigation of the device 100 to the desired location. Such a configuration may also place the inner tubular member 110 in tension while the distal holding section 108 applies a compression force on the outer tubular member 102, as will be discussed in more detail below. As discussed above, a locking mechanism 132 in the handle assembly 120 may be utilized to releasably maintain the outer tubular member 102 and the inner tubular member 110 in a desired orientation.

Figure 4:
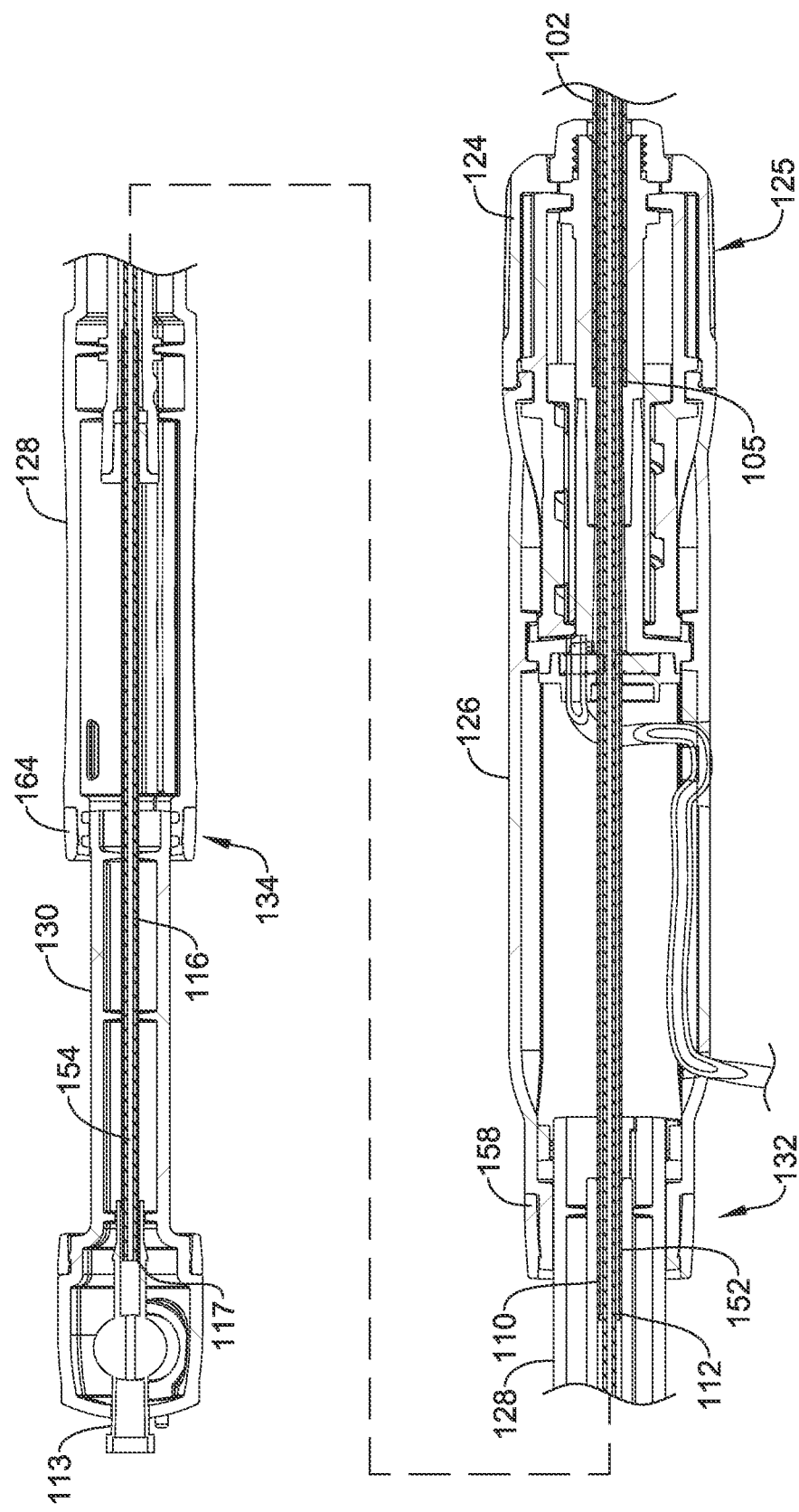
FIG. 4 is a cross-sectional side view of the proximal portion of the delivery device of FIG. 2.

FIG. 4 illustrates a cross-sectional view of the handle assembly 120 of the delivery device. As discussed above, the handle assembly 120 may include a first hub portion 126 attached to the proximal end section 104 of the outer tubular member 102, a second hub portion 128 attached to a proximal end section of the inner tubular member 110, and a third hub portion 130 attached to a proximal end section of a push member 116. Each of the first hub portion 126, the second hub portion 128, and the third hub portion 130 may be slidable and rotatable relative to each other such that the outer tubular member 102, inner tubular member 110, and push member 116 may be individually actuated.

The push member 116 may extend distally from a proximal end 117. The proximal end 117 of the push member 116 may be positioned within or adjacent to a valve member 113. The valve member 113 may be in fluid communication with a lumen 154 of the push member 116. The lumen 154 may extend from the proximal end 117 to the distal portion 118 for delivering fluids, such as, but not limited to, a contrast and/or flushing fluid to the cavity 142 of the distal holding section 108. In some instances, the push member 116 may be coupled or affixed to the third hub portion 130 adjacent the proximal end 117 of the push member 116, although this is not required. It is contemplated that the push member 116 may be affixed to the third hub portion 130 at any longitudinal location desired. In some instances, a tether (not explicitly shown) for securing the implantable device 10 to the distal portion 118 of the push member 116 may be disposed within the lumen 154 and may exit the device 100 through valve member 113, although this is not required.

The inner tubular member 110 may extend distally from a proximal end 112. The proximal end 112 of the inner tubular member 110 may be positioned within the second hub portion 128. The inner tubular member 110 may include a lumen 152 extending from the proximal end 112 to a distal end of the inner tubular member 110. The push member 116 may be slidably disposed within the lumen 152 of the inner tubular member 110. In some instances, the inner tubular member 110 may be coupled or affixed to the second hub portion 128 adjacent the proximal end 112 of the push inner tubular member 110, although this is not required. It is contemplated that the inner tubular member 110 may be affixed to the second hub portion 128 at any longitudinal location desired.

The outer tubular member 102 may extend distally from a proximal end 105. The proximal end 105 of the outer tubular member 102 may be positioned within the first hub portion 126. The outer tubular member 102 may include a lumen 150 extending from the proximal end 105 to a distal end 103 of the outer tubular member 102. The inner tubular member 110 may be slidably disposed within the lumen 150 of the outer tubular member 102. In some instances, the outer tubular member 102 may be coupled or affixed to the first hub portion 126 adjacent the proximal end 105 of the outer tubular member 102, although this is not required. It is contemplated that the outer tubular member 102 may be affixed to the first hub portion 126 at any longitudinal location desired.

In some instances, the first hub portion 126 may include a retaining ring 158 positioned adjacent to a proximal end of the first hub portion 126. In some instances, the retaining ring 158 may be rotatable about a longitudinal axis of the handle assembly 120. It is further contemplated that the retaining ring 158 may include locking features configured to engage with other locking features of the locking mechanism 132. In some instances, the second hub portion 128 may include a retaining ring 164 positioned adjacent to a proximal end of the second hub portion 128. In some instances, the retaining ring 164 may be rotatable about a longitudinal axis of the handle assembly 120. It is further contemplated that the retaining ring 164 may include locking features configured to engage with other locking features of the locking mechanism 134.

Figure 5:
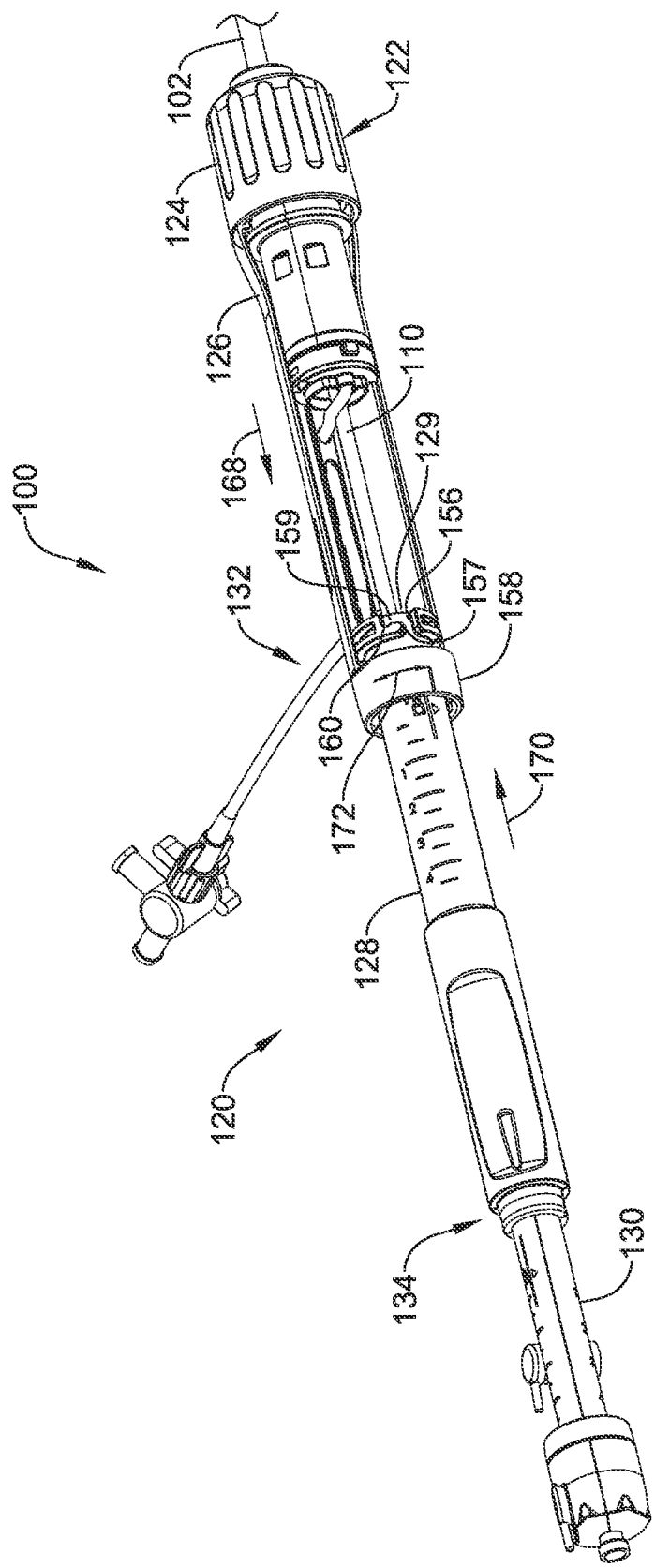
FIG. 5 is a perspective view of the proximal portion of the delivery device of FIG. 2 with portions removed.

FIG. 5 illustrates a partial perspective view of handle assembly 120 with portions of the first hub portion 126 removed to more clearly illustrate features of the first locking mechanism 132, which may releasably couple the first hub portion and the second hub portion and/or the outer tubular member 102 and the inner tubular member 110. In some instances, the locking mechanism 132 may be a bayonet style locking feature. It is contemplated that a generally "L" shaped groove 156 may be formed in the second hub portion 128 adjacent a distal end 129 of the second hub portion 128. In some instances, the retaining ring 158 may include a protrusion 162 (schematically represented in FIGS. 6A-6E) extending radially inward from an inner surface of the retaining ring 158. The retaining ring 158, and the first hub portion 126, may have an inner diameter generally larger than an outer diameter of the second hub portion 128 such that the second hub portion 128 can be proximally refracted 168 and distally advanced 170 within a lumen of the first hub portion 126.

Referring additionally to FIGS. 6A-6E, when a user desires to couple the outer tubular member 102 and the inner tubular member 110, the second hub portion 128 may be rotated 172 relative to the first hub portion 126 about the longitudinal axis of the handle assembly 120 to align the protrusion 162 with a first or vertical portion 157 of the groove 156 as shown in FIG. 6A. The use of "vertical" and "horizontal" are not intended to be limiting rather to provide relative movements of interacting components. In alternative embodiments, the first hub portion 126, or components thereof, may be rotated relative to the second hub portion 128. The second hub portion 128 may be proximally retracted 168 to advance the protrusion 162 further into the groove 156 as indicated at arrow 174. Once the protrusion 162 is positioned distal of protruding region 176, the second hub portion 128 may be rotated in a first direction to advance the protrusion 162 along a second or horizontal portion 159 of the groove 156 generally orthogonal to the vertical portion 157 towards a dip, recess, or serif 160 positioned at an end of the horizontal portion 159 as shown at arrow 178 in FIG. 6B. A wall 180 may provide a stopping mechanism adjacent to the serif 160. Once the protrusion 162 has engaged the stopping mechanism 180, the second hub portion 128 may be advanced distally 170 to secure the protrusion 162 within the serif 160, as shown in FIG. 6C. The serif 160 may help prevent accidental rotation of the retaining ring 158 and thus accidental uncoupling of the outer tubular member 102 and the inner tubular member 110.

It is contemplated that in an unbiased state or unlocked configuration, (e.g. when the outer tubular member 102 and the inner tubular member 110 are not coupled via the locking mechanism 132) the distal end 129 of the second hub portion 128 may extend distally beyond the protrusion 162 and the retaining ring 158. Proximally retracting the second hub portion 128 (secured to the inner tubular member 110) relative to the first hub portion 126 (secured to the outer tubular member 102) to engage the protrusion 162 and the serif 160 may place the inner tubular member 110 in tension.

In some instances, a tensile force in the range of about 1-3 pounds-force (about 4.4-13.3 Newtons) or approximately less than 2 pounds-force (approximately less than 8.9 Newtons) may be applied to the inner tubular member 110. As the inner tubular member 110 (e.g., the proximal end of the inner tubular member 110) is proximally retracted along with the second hub portion 128, the hub portion 136 of the distal holding section 108 may apply a proximal force on the distal end of the outer tubular member 102 thus placing the outer tubular member 102 under compression. This configuration may allow the multiple shaft delivery device 100 to behave like a single shaft delivery device. It is contemplated that placing the inner tubular member 110 in tension may account for a shorter path length of the outer tubular member 102 at bends in the delivery device 100. For example, as the outer tubular member 102 curves a first side of the tube wall may have a first arc radius and a second side of the tube wall, opposite first side of the tube wall, may have a second arc radius smaller than the first arc radius. In an uncoupled configuration, the inner tubular member 110 may contact the first side of the tube wall of the outer tubular member 102. This may place a biasing force against the outer tubular member 102 in a direction other than the desired curve. In a coupled arrangement with the inner tubular member 110 in tension, the position of the inner tubular member 110 within the lumen 150 of the outer tubular member 102 may be brought closer the second side of the tube wall. This may facilitate steering of the device 100 to the desired location by reducing the forces applied on the outer tubular member 102. Additionally, actuation of either of the outer tubular member 102 or the inner tubular member 110 may result in the actuation of both the outer tubular member 102 and the inner tubular member 110. It is further contemplated that when the inner tubular member 110 and the outer tubular member 102 are in a coupled configuration, the distal holding section 108 may not move distally out of engagement with the outer tubular member 102.

When a user desires to uncouple the outer tubular member 102 and the inner tubular member 110, the second hub portion 128 may be distally advanced 170 to disengage the protrusion 162 from the serif 160. The second hub portion 128 may then be rotated 172 relative to the first hub portion 126 about the longitudinal axis of the handle assembly 120 in a direction opposite to the direction used to couple the outer tubular member 102 and the inner tubular member 110 as indicated at arrow 182 in FIG. 6D. The second hub portion 128 may be rotated in a second direction, generally opposite to the first direction, to advance the protrusion 162 along the horizontal portion 159 of the groove 156 towards the vertical portion 157 as shown at arrow 182 in FIG. 6D. A wall 184 may provide a stopping mechanism adjacent to the vertical portion 157. Once the protrusion 162 has engaged the stopping mechanism 184, the second hub portion 128 may be advanced distally 170 to disengage the protrusion 162 from the mating groove 156, as shown at arrow 186 in FIG. 6E. It is further contemplated that the outer surface of the retaining ring 158, the first hub portion 126, and/or the second hub portion 128 may be provided with visual markings to assist the user locking and/or unlocking the locking mechanism 132. It is further contemplated that in some instances, the "L" shaped groove may be positioned on the retaining ring 158 or first hub portion 126 and the protrusion 162 may be positioned on the second hub portion 128. Furthermore, while the first locking mechanism 132 has been described as a bayonet style locking mechanism other locking mechanisms capable of releasably securing the outer tubular member 102 and the inner tubular member 110 are contemplated.

For example, the locking mechanism 132 may be formed in a similar manner to a quick connect locking mechanism commonly used in plumbing applications. A quick connect locking mechanism may utilize an o-ring and a compression fit to maintain a fluid tight seal. A rotating locking ring may maintain the quick connect locking mechanism in a locked configuration. In other embodiments, the locking mechanism 132 may include a threaded engagement similar to the threaded engagement described above with respect to FIG. 3A. For example, the retaining ring 158 or other portion of the first hub portion 126 may include a first threaded region and the second hub portion 128 may include a second threaded region configured to mate with and/or threadably engage the threaded region on the retaining ring 158 or other portion of the first hub portion 126. Thus rotation of the retaining ring 158 and/or other portion of the first hub portion 126 relative to the second hub portion 128 may place the inner tubular member 110 in tension while placing the outer tubular member 102 in compression. In yet other embodiments, the locking mechanism 132 may include a snap lock, a tongue and groove type lock, a mating detent and groove or other features configured to engage a corresponding feature on the retaining ring 158 and/or second hub portion 128 similar to the coupling arrangement described above with respect to FIG. 3B.

Figure 7:
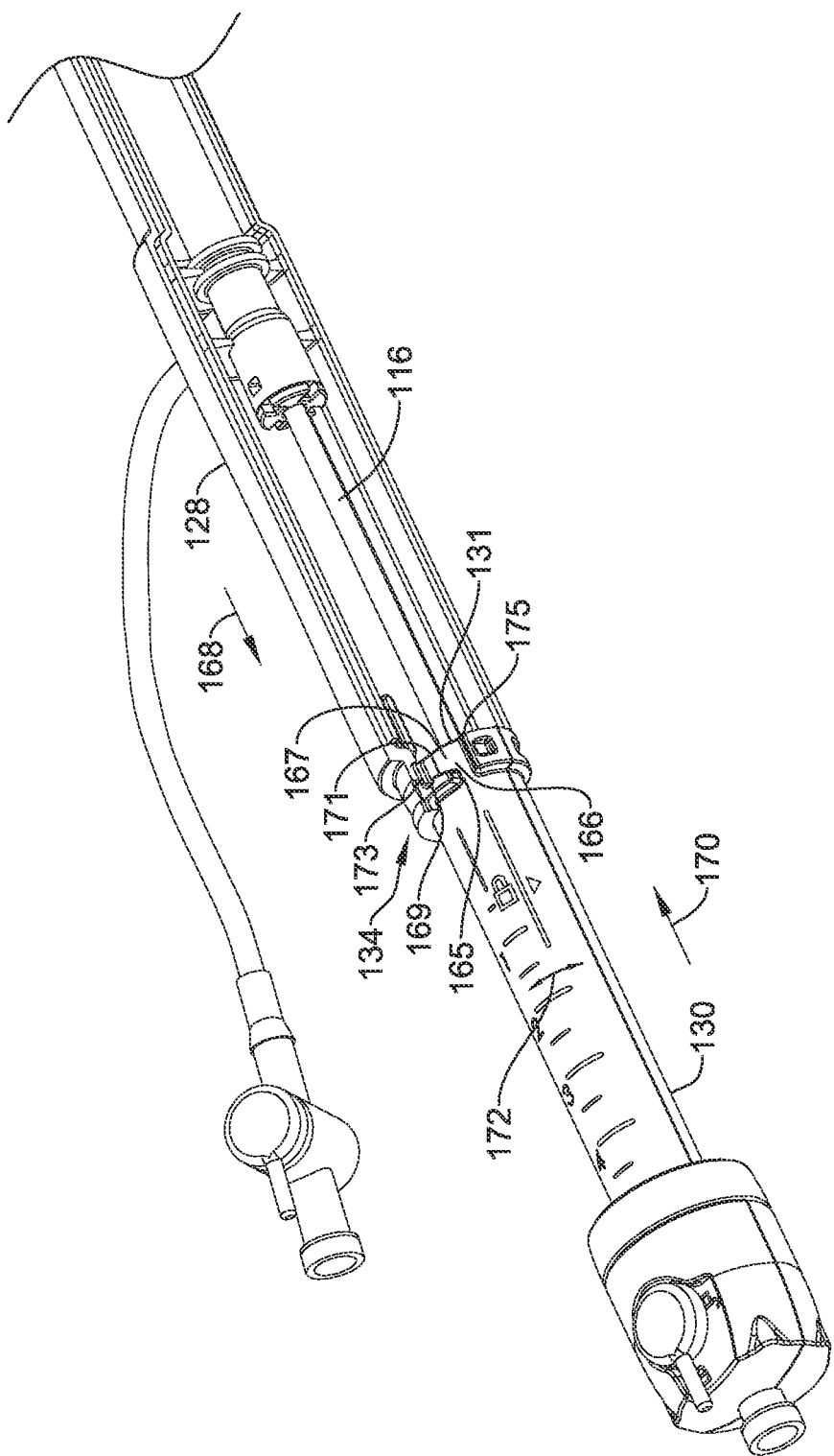
FIG. 7 is a perspective view of the proximal portion of the delivery device of FIG. 2 with portions removed.

FIG. 7 illustrates another partial perspective view of handle assembly 120 with portions of the second hub portion 128 removed to more clearly illustrate features of the second locking mechanism 134, which may be used to releasably couple the inner tubular member 110 and the push member 116. In some instances, the locking mechanism 134 may be a bayonet style locking feature. It is contemplated that a generally "L" shaped groove 166 may be formed in the third hub portion 130 adjacent a distal end 131 of the third hub portion 130. In some instances, the retaining ring 164 (not explicitly shown in FIG. 7) may include a protrusion, which may be similar in form and function to the protrusion 162 described with respect to FIGS. 5 and 6A-6E, extending radially inward from an inner surface of the retaining ring 164. The retaining ring 164, and the second hub portion 128, may have an inner diameter generally larger than an outer diameter of the third hub portion 130 such that the third hub portion 130 can be proximally retracted 168 and distally advanced 170 within a lumen of the second hub portion 128. It is contemplated that the second locking mechanism 134 may function in a similar manner to the first locking mechanism 132 described above.

When a user desires to couple the inner tubular member 110 and the push member 116, the third hub portion 130 may be rotated 172 relative to the second hub portion 128 in a first direction about the longitudinal axis of the handle assembly 120 to align the protrusion with a first or vertical portion 165 of the groove 166. The use of "vertical" and "horizontal" are not intended to be limiting rather to provide relative movements of interacting components. In alternative embodiments, the second hub portion 128, or components thereof, may be rotated relative to the third hub portion 128. The third hub portion 130 may be proximally refracted 168 to advance the protrusion further into the groove 166. Once the protrusion is positioned distal of protruding region 171, the third hub portion 130 may be rotated to advance the protrusion along a second or horizontal portion 167 of the groove 166 generally orthogonal to the vertical portion 165 towards a dip or serif 169 positioned at an end of the horizontal portion 167. A wall 173 may provide a stopping mechanism adjacent to the serif 169. Once the protrusion has engaged the stopping mechanism 173, the third hub portion 130 may be advanced distally 170 to secure the protrusion within the serif 169. The serif 169 may help prevent accidental rotation of the retaining ring 164 and thus accidental uncoupling of the inner tubular member 110 and the push member 116.

It is contemplated that in an unbiased state or unlocked configuration, (e.g. when the inner tubular member 110 and the push member 116 are not coupled via the locking mechanism 134) the distal end 131 of the third hub portion 130 may extend distally beyond the protrusion and the retaining ring 164. Proximally retracting the third hub portion 130 (secured to the push member 116) relative to the second hub portion 128 (secured to the inner tubular member 110) to engage the protrusion and the serif 169 may place the push member 116 in tension. It is contemplated that placing the push member 116 in tension may account for a shorter path length at bends in the delivery device 100.

When a user desires to uncouple the inner tubular member 110 and the push member 116, the third hub portion 130 may be distally advanced 170 to disengage the protrusion from the serif 169. The third hub portion 130 may then be rotated 172 relative to the second hub portion 128 in a second direction, generally opposite the first direction, about the longitudinal axis of the handle assembly 120. The third hub portion 130 may be rotated to advance the protrusion along the horizontal portion 167 of the groove 166 towards the vertical portion 165. A wall 175 may provide a stopping mechanism adjacent to the vertical portion 165. Once the protrusion has engaged the stopping mechanism 175, the third hub portion 130 may be advanced distally 170 to disengage the protrusion from the mating groove 166. It is further contemplated that the outer surface of the retaining ring 164, second hub portion 128, and/or the third hub portion 130 may be provided with visual markings to assist the user locking and/or unlocking the locking mechanism 134. It is further contemplated that in some instances, the "L" shaped groove may be positioned on the retaining ring 164 or second hub portion 128 and the protrusion may be positioned on the third hub portion 130. Furthermore, while the second locking mechanism 134 has been described as a bayonet style locking mechanism other locking mechanisms capable of releasably securing the inner tubular member 110 and the push member 116 are contemplated.

For example, the locking mechanism 134 may be formed in a similar manner to a quick connect locking mechanism commonly used in plumbing applications. A quick connect locking mechanism may utilize an o-ring and a compression fit to maintain a fluid tight seal. A rotating locking ring may maintain the quick connect locking mechanism in a locked configuration. In other embodiments, the locking mechanism 134 may include a threaded engagement similar to the threaded engagement described above with respect to FIG. 3A. For example, the retaining ring 164 or other portion of the second hub portion 128 may include a first threaded region and the third hub portion 130 may include a second threaded region configured to mate with and/or threadably engage the threaded region on the retaining ring 164 or other portion of the second hub portion 128. Thus rotation of the retaining ring 164 and/or other portion of the second hub portion 128 relative to the third hub portion 130 may place the push member 116 in tension. In yet other embodiments, the locking mechanism 134 may include a snap lock, a tongue and groove type lock, a mating detent and groove or other features configured to engage a corresponding feature on the retaining ring 164 and/or third hub portion 130 similar to the coupling arrangement described above with respect to FIG. 3B.

The materials that can be used for the various components of the delivery devices, such as delivery device 100 (and/or other delivery structures disclosed herein) and the various members disclosed herein may include those commonly associated with medical devices. For simplicity purposes, the following discussion makes reference the delivery device 100 and components of thereof. However, this is not intended to limit the devices and methods described herein, as the discussion may be applied to other similar delivery systems and/or components of delivery systems or devices disclosed herein.

The delivery device 100 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY®

ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery device 100 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

In some embodiments, a degree of Magnetic Resonance Imaging (MRI) compatibility is imparted into the delivery device 100. For example, delivery device 100 or portions or components thereof, may be made of a material that does not substantially distort the image and create substantial artifacts (i.e., gaps in the image). Certain ferromagnetic materials, for example, may not be suitable because they may create artifacts in an MRI image. The delivery device 100, or portions thereof, may also include and/or be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A delivery device for delivering an implantable leadless pacing device, the delivery device comprising:
   an outer tubular member including a lumen extending from a proximal end to a distal end thereof;
   an inner tubular member including a lumen extending from a proximal end to a distal end thereof, the inner tubular member slidably disposed within the lumen of the outer tubular member;
   a distal holding section extending distally of a distal end of the inner tubular member, the distal holding section defining a cavity therein for receiving an implantable leadless pacing device;
   a handle assembly including at least a first hub portion affixed adjacent to the proximal end of the outer tubular member and a second hub portion affixed adjacent to the proximal end of the inner tubular member, the first hub portion including a lumen extending therein and at least a portion of the second hub portion slidably and rotatably disposed within the lumen of the first hub portion; and a first locking mechanism having a first engaging feature on the first hub portion and a second engaging feature on the second hub portion, the first and second engaging features configured to be releasably and directly coupled together within the lumen of the first hub portion of the handle assembly;

wherein the first locking mechanism is configured to releasably couple the first hub portion and the second hub portion.

2. The delivery device of claim 1, wherein the first locking mechanism has a locked position and an unlocked position wherein the inner tubular member is held in tension in the locked position.

3. The delivery device of claim 2, wherein the outer tubular member is held in compression in the locked position.

4. The delivery device of claim 1, wherein the first hub portion and the second hub portion are individually slidable and rotatable when the first locking mechanism is in an unlocked configuration.

5. The delivery device of claim 1, wherein the first locking mechanism comprises a bayonet style locking mechanism.

6. The delivery device of claim 5, wherein the second hub portion comprises a groove positioned adjacent a distal end of the second hub portion, the groove configured to receive an inwardly extending protrusion of the first hub portion.

7. The delivery device of claim 6, wherein the groove comprises a first portion, a second portion extending generally orthogonal to the first portion, and a serif positioned at an end of the second portion.

8. The delivery device of claim 7, wherein disposing the protrusion within the serif releasably couples the outer tubular member and the inner tubular member such that longitudinal or rotational actuation of either of the outer tubular member or the inner tubular member results in corresponding actuation of both the outer tubular member and the inner tubular member.

9. The delivery device of claim 7, wherein disposing the protrusion within the serif places the inner tubular member in tension and the outer tubular member in compression.

10. The delivery device of claim 1, further comprising a push member slidably disposed within the lumen of the inner tubular member.

11. The delivery device of claim 10, further comprising a third hub portion affixed adjacent to a proximal end of the push member.

12. The delivery device of claim 11, further comprising a second locking mechanism disposed within the handle assembly.

13. The delivery device of claim 12, wherein the third hub portion is slidable and rotatable independent of either of the first hub portion or the second hub portion when the second locking mechanism is in an unlocked configuration.

14. The delivery device of claim 1, wherein the first locking mechanism is selected from the group of a snap lock, a threaded engagement, or a quick connect locking feature.

15. A delivery device for delivering an implantable leadless pacing device, the delivery device comprising:

an outer tubular member including a lumen extending from a proximal end to a distal end thereof;

an inner tubular member including a lumen extending from a proximal end to a distal end thereof, the inner tubular member slidably disposed within the lumen of the outer tubular member;

a push member having a proximal end and a distal end, the push member slidably disposed within the lumen of the inner tubular member;

a distal holding section extending distally of a distal end of the inner tubular member, the distal holding section defining a cavity therein for receiving an implantable leadless pacing device;

a handle assembly including a distal hub portion affixed adjacent to the proximal end of the outer tubular member, an intermediate hub portion affixed adjacent to the proximal end of the inner tubular member, and a proximal hub portion affixed adjacent to the proximal end of the push member, a distal end portion of the intermediate hub portion slidably and rotatably disposed within a lumen of the distal hub portion and a distal end portion of the proximal hub portion slidably and rotatably disposed within a lumen of the intermediate hub portion such that the distal hub portion, the intermediate hub portion, and the proximal hub portion are arranged in a telescoping configuration such that each of the distal hub portion, intermediate hub portion, and proximal hub portion are capable of being longitudinally and rotationally actuated individually; and a first locking mechanism positioned within the lumen of the distal hub portion and disposed between the distal hub portion and the intermediate hub portion;

wherein the first locking mechanism is configured to releasably couple the distal hub portion and the intermediate hub portion.

16. The delivery device of claim 15, wherein the first locking mechanism is user actuatable between an unlocked configuration and a locked configuration.

17. The delivery device of claim 16, wherein when in the locked configuration, the intermediate hub portion is proximally retracted to place the inner tubular member in tension and the outer tubular member in compression.

18. A delivery device for delivering an implantable leadless pacing device, the delivery device comprising:

an outer tubular member including a lumen extending from a proximal end to a distal end thereof;

an inner tubular member including a lumen extending from a proximal end to a distal end thereof, the inner tubular member slidably disposed within the lumen of the outer tubular member;

a distal holding section secured to and extending distally of a distal end of the inner tubular member, the distal holding section defining a cavity therein for receiving an implantable leadless pacing device;

a push member having a proximal end and a distal end, the push member slidably disposed within the lumen of the inner tubular member;

a handle assembly including at least a first hub portion affixed adjacent to the proximal end of the outer tubular member, a second hub portion affixed adjacent to the proximal end of the inner tubular member, and a third hub portion affixed adjacent to the proximal end of the push member, the first hub portion, the second hub portion, and the third hub portion each selectively longitudinally movable relative to each other; and a first locking mechanism configured to releasably lock the first hub portion to the second hub portion, the first locking mechanism having a locked position and an unlocked position, wherein in the unlocked position of the first locking mechanism the first hub portion is longitudinally movable relative to the second hub portion; and a second locking mechanism configured to releasably lock the second hub portion to the third hub portion, the second locking mechanism having a locked position and an unlocked position, wherein in the unlocked position of the second locking mechanism the second hub portion is longitudinally movable relative to the third hub portion;

wherein in the locked position of the first locking mechanism the inner tubular member is held in tension and the outer tubular member is held in compression.

19. The delivery device of claim 18, wherein the second hub portion extends proximal of the first hub portion, and the third hub portion extends proximal of the second hub portion.

20. The delivery device of claim 19, wherein a distal end portion of the second hub portion is slidably and rotatably disposed within a lumen of the first hub portion and a distal end portion of the third hub portion is slidably and rotatably disposed within a lumen of the second hub portion such that the first hub portion, the second hub portion, and the third hub portion are arranged in a telescoping configuration.

* * * * *